US011633609B2

(12) United States Patent
Shahandeh et al.

(10) Patent No.: US 11,633,609 B2
(45) Date of Patent: *Apr. 25, 2023

(54) SYSTEM AND METHODS FOR ESTABLISHING A COMMUNICATION SESSION BETWEEN AN IMPLANTABLE MEDICAL DEVICE AND AN EXTERNAL DEVICE

(71) Applicant: Pacesetter, Inc., Sylmar, CA (US)

(72) Inventors: Reza Shahandeh, Thousand Oaks, CA (US); Richard Williamson, Los Angeles, CA (US); Gabriel Mouchawar, Valencia, CA (US); Brent Croft, Lewisville, TX (US); William Winstrom, Georgetown, TX (US); Robert McCormick, Frisco, TX (US); Jorge N. Amely-Velez, Simi Valley, CA (US); Thanh Tieu, Simi Valley, CA (US); Ali Dianaty, Northridge, CA (US); Samir Shah, Valencia, CA (US); Yongjian Wu, Saratoga, CA (US)

(73) Assignee: Pacesetter, Inc., Sylmar, CA (US)

( * ) Notice: Subject to any disclaimer, the term of this patent is extended or adjusted under 35 U.S.C. 154(b) by 303 days.

This patent is subject to a terminal disclaimer.

(21) Appl. No.: 17/086,739

(22) Filed: Nov. 2, 2020

(65) Prior Publication Data
US 2021/0046323 A1 Feb. 18, 2021

Related U.S. Application Data

(60) Division of application No. 15/860,507, filed on Jan. 2, 2018, now Pat. No. 11,007,370, which is a
(Continued)

(51) Int. Cl.
*A61N 1/08* (2006.01)
*A61N 1/372* (2006.01)
(Continued)

(52) U.S. Cl.
CPC ..... *A61N 1/37252* (2013.01); *A61N 1/36514* (2013.01); *A61N 1/37217* (2013.01);
(Continued)

(58) Field of Classification Search
None
See application file for complete search history.

(56) References Cited

U.S. PATENT DOCUMENTS 5,095,308 A  3/1992 Hewitt
5,475,372 A  12/1995 Burke
(Continued)

FOREIGN PATENT DOCUMENTS

AU  2011224323 B2  9/2011
EP  2878334 B1  3/2017
(Continued)

OTHER PUBLICATIONS

Restriction Requirement for corresponding U.S. Appl. No. 15/676,571 dated Sep. 26, 2018.
(Continued)

*Primary Examiner* — Jon Eric C Morales
(74) *Attorney, Agent, or Firm* — The Small Patent Law Group LLC; Dean D. Small

(57) ABSTRACT

A method is provided for establishing a communication session with an implantable medical device ("IMD"). The method includes configuring an IMD and an external device to communicate with one another through a protocol that utilizes a dedicated advertisement channel. The advertisement period and the scan period of the protocol are independent of one another such that the advertisement and scan periods at least partially overlap intermittently after a number of cycles. When the external device detects one of the
(Continued)

advertisement notices, the method includes establishing a communications link between the external device and the IMD.

20 Claims, 7 Drawing Sheets

Related U.S. Application Data continuation of application No. 15/433,771, filed on Feb. 15, 2017, now Pat. No. 9,855,433, and a continuation of application No. 15/154,787, filed on May 13, 2016, now Pat. No. 9,572,992, and a continuation of application No. 14/091,809, filed on Nov. 27, 2013, now abandoned.

(51) Int. Cl.
  *A61N 1/39* (2006.01)
  *H04W 76/10* (2018.01)
  *H04L 65/1069* (2022.01)
  *H04W 4/80* (2018.01)
  *H04W 8/00* (2009.01)
  *A61N 1/365* (2006.01)

(52) U.S. Cl.
  CPC ...... *A61N 1/39622* (2017.08); *H04L 65/1069* (2013.01); *H04W 4/80* (2018.02); *H04W 8/005* (2013.01); *H04W 76/10* (2018.02)

(56) References Cited

U.S. PATENT DOCUMENTS

| | | | |
|---|---|---|---|
| 5,746,697 A | 5/1998 | Swedlow et al. | |
| 5,919,216 A | 7/1999 | Houben et al. | |
| 5,924,979 A | 7/1999 | Swedlow et al. | |
| 6,002,671 A | 12/1999 | Kahkosha et al. | |
| 6,200,265 B1 | 3/2001 | Walsh et al. | |
| 6,480,476 B1 | 11/2002 | Willars | |
| 6,564,104 B2 | 5/2003 | Nelson et al. | |
| 7,110,823 B2 | 9/2006 | Whitehurst et al. | |
| 7,653,017 B2 | 1/2010 | Huylebroeck | |
| 7,656,853 B2 | 2/2010 | Albulet | |
| 7,729,776 B2 | 6/2010 | Von Arx et al. | |
| 7,899,401 B2 | 3/2011 | Tanaka et al. | |
| 7,957,813 B1 | 6/2011 | Persson et al. | |
| 7,987,378 B2 | 7/2011 | Lee et al. | |
| 7,999,655 B2 | 8/2011 | Yoshikawa | |
| 8,145,320 B2 | 3/2012 | Condorf et al. | |
| 8,172,766 B1 | 5/2012 | Kayyali et al. | |
| 8,386,051 B2 | 2/2013 | Rys | |
| 8,412,946 B2 | 4/2013 | Lee et al. | |
| 8,428,528 B2 | 4/2013 | Sutton et al. | |
| 8,475,372 B2 | 7/2013 | Schell et al. | |
| 8,744,572 B1 | 6/2014 | Greenhut et al. | |
| 8,750,976 B2 | 6/2014 | Stadler et al. | |
| 8,838,251 B2 | 9/2014 | Haubrich et al. | |
| 8,929,995 B2 | 1/2015 | Stancer et al. | |
| 8,959,368 B2 | 2/2015 | Lee et al. | |
| 9,009,805 B1 | 4/2015 | Kirkby et al. | |
| 9,072,913 B2 | 7/2015 | Jacobson | |
| 9,072,914 B2 | 7/2015 | Greenhut et al. | |
| 9,168,383 B2 | 10/2015 | Jacobson et al. | |
| 9,288,614 B1 | 3/2016 | Young et al. | |
| 9,427,592 B2 | 8/2016 | Wu et al. | |
| 9,431,694 B2 | 8/2016 | Li et al. | |
| 9,445,051 B1 | 9/2016 | Muthsandra Kantharaju et al. | |
| 9,445,264 B2 | 9/2016 | Young et al. | |
| 9,572,992 B2 | 2/2017 | Shahandeh et al. | |
| 9,687,658 B2 | 6/2017 | Wu et al. | |
| 9,833,628 B2 | 12/2017 | Yoder et al. | |
| 9,844,676 B2 | 12/2017 | Zhang et al. | |
| 9,855,433 B2 | 1/2018 | Shahandeh et al. | |
| 9,894,691 B1 | 2/2018 | Hellman et al. | |
| 9,913,989 B2 | 3/2018 | Schilling et al. | |
| 9,949,660 B2 | 4/2018 | Weinberg et al. | |
| 9,980,140 B1 | 5/2018 | Spencer et al. | |
| 10,055,567 B2 | 8/2018 | Ulrich et al. | |
| 10,086,208 B2 | 10/2018 | Hoffman et al. | |
| 10,112,045 B2 | 10/2018 | Anderson et al. | |
| 10,124,182 B2 | 11/2018 | Kivi et al. | |
| 10,201,712 B2 | 2/2019 | Yoder et al. | |
| 10,278,217 B2 | 4/2019 | Wu et al. | |
| 10,305,692 B2 | 5/2019 | Peterson | |
| 10,307,599 B2 | 6/2019 | Schilling et al. | |
| 10,449,372 B2 | 10/2019 | Wu et al. | |
| 10,471,267 B2 | 11/2019 | Thompson-Nauman et al. | |
| 10,493,287 B2 | 12/2019 | Yoder et al. | |
| 10,504,125 B2 | 12/2019 | Harvey | |
| 10,575,346 B2 | 2/2020 | Wu et al. | |
| 10,576,290 B2 | 3/2020 | Schilling et al. | |
| 10,582,444 B1 | 3/2020 | Young et al. | |
| 10,617,875 B2 | 4/2020 | Demmer et al. | |
| 10,639,488 B2 | 5/2020 | Kalgren et al. | |
| 10,792,490 B2 | 10/2020 | Seifert et al. | |
| 11,007,370 B2 * | 5/2021 | Shahandeh ............. H04W 4/80 |
| 2002/0123672 A1 | 9/2002 | Christophersom et al. | |
| 2003/0055464 A1 | 3/2003 | Darvish et al. | |
| 2003/0171791 A1 | 9/2003 | KenKnight et al. | |
| 2003/0208242 A1 | 11/2003 | Harel et al. | |
| 2003/0229383 A1 | 12/2003 | Whitehurst et al. | |
| 2004/0006492 A1 | 1/2004 | Watanabe | |
| 2004/0113771 A1 | 6/2004 | Ozaki et al. | |
| 2005/0283208 A1 | 12/2005 | Von Arx et al. | |
| 2006/0128308 A1 | 6/2006 | Michael et al. | |
| 2008/0161660 A1 | 7/2008 | Ameson et al. | |
| 2008/0167531 A1 | 7/2008 | McDermott | |
| 2008/0232405 A1 | 9/2008 | Gallo | |
| 2008/0262573 A1 | 10/2008 | Seeberger et al. | |
| 2009/0216100 A1 | 8/2009 | Ebner et al. | |
| 2009/0264964 A1 | 10/2009 | Abrahamson | |
| 2010/0106224 A1 | 4/2010 | Von Arx et al. | |
| 2010/0315225 A1 | 12/2010 | Teague | |
| 2011/0153420 A1 | 6/2011 | Harvey | |
| 2011/0184491 A1 | 7/2011 | Kivi | |
| 2011/0202113 A1 | 8/2011 | Persson et al. | |
| 2012/0044810 A1 | 2/2012 | Koto et al. | |
| 2012/0101544 A1 | 4/2012 | Hoberman et al. | |
| 2012/0108922 A1 | 5/2012 | Schell et al. | |
| 2012/0172690 A1 | 7/2012 | Anderson et al. | |
| 2012/0172941 A1 | 7/2012 | Rys | |
| 2012/0182917 A1 | 7/2012 | Edlund | |
| 2012/0215286 A1 | 8/2012 | Rahman | |
| 2012/0220351 A1 | 8/2012 | Kerai et al. | |
| 2012/0271902 A1 | 10/2012 | Baliga et al. | |
| 2012/0313760 A1 | 12/2012 | Okano | |
| 2013/0079836 A1 | 3/2013 | Srivastava et al. | |
| 2013/0109989 A1 | 5/2013 | Busse et al. | |
| 2013/0165819 A1 | 6/2013 | Tieu | |
| 2013/0214909 A1 | 8/2013 | Meijers et al. | |
| 2014/0113558 A1 | 4/2014 | Varoglu et al. | |
| 2014/0133656 A1 | 5/2014 | Wurster et al. | |
| 2014/0188348 A1 | 7/2014 | Gautama et al. | |
| 2014/0214104 A1 | 7/2014 | Greenhut et al. | |
| 2014/0274127 A1 | 9/2014 | Beidel | |
| 2014/0330327 A1 | 11/2014 | Thompson-Nauman et al. | |
| 2014/0370917 A1 | 12/2014 | Buchheim et al. | |
| 2015/0065047 A1 | 3/2015 | Wu et al. | |
| 2015/0099467 A1 | 4/2015 | Kang | |
| 2015/0119077 A1 | 4/2015 | Buchheim et al. | |
| 2015/0133951 A1 | 5/2015 | Seifert et al. | |
| 2015/0148868 A1 | 5/2015 | Shahandeh et al. | |
| 2015/0255858 A1 | 9/2015 | Li et al. | |
| 2015/0265843 A1 | 9/2015 | Wu et al. | |
| 2015/0296329 A1 | 10/2015 | Mao et al. | |
| 2015/0341785 A1 | 11/2015 | Young et al. | |
| 2016/0007873 A1 | 1/2016 | Huelskamp et al. | |
| 2016/0134709 A1 | 5/2016 | Savolainen | |
| 2016/0255456 A1 | 9/2016 | Lee et al. | |
| 2016/0259855 A1 | 9/2016 | Jwa et al. | |
| 2016/0278016 A1 | 9/2016 | Wang et al. | |
| 2016/0327631 A1 | 11/2016 | Salokannel et al. | |

(56) References Cited

U.S. PATENT DOCUMENTS

| | | |
|---|---|---|
| 2017/0026777 A1 | 1/2017 | Denboer et al. |
| 2017/0265080 A1 | 9/2017 | Azam et al. |
| 2017/0309166 A1 | 10/2017 | Abrahamson |
| 2017/0312530 A1 | 11/2017 | Schilling et al. |
| 2018/0021589 A1 | 1/2018 | Wu et al. |
| 2018/0028827 A1 | 2/2018 | Schilling et al. |
| 2018/0078777 A1 | 3/2018 | Wu et al. |
| 2018/0243567 A1 | 8/2018 | St. Martin et al. |
| 2018/0243568 A1 | 8/2018 | Demmer et al. |
| 2018/0243577 A1 | 8/2018 | Kivi et al. |
| 2018/0288147 A1 | 10/2018 | Shanmugam et al. |
| 2018/0295660 A1 | 10/2018 | Choi et al. |
| 2019/0021954 A1 | 1/2019 | Lanigan, Jr. et al. |
| 2019/0191468 A1 | 6/2019 | Wu et al. |
| 2020/0094062 A1 | 3/2020 | Yoder et al. |
| 2020/0306543 A1 | 10/2020 | Boor et al. |

FOREIGN PATENT DOCUMENTS

| | | |
|---|---|---|
| EP | 2991239 B1 | 10/2017 |
| EP | 2457332 B | 1/2019 |
| WO | 03008013 A2 | 1/2003 |
| WO | 2010087864 A1 | 8/2010 |
| WO | 2011034468 A | 3/2011 |
| WO | 2011094075 A3 | 8/2011 |
| WO | 2014035494 A1 | 3/2014 |
| WO | 2015069797 A1 | 5/2015 |
| WO | 2018156386 A1 | 8/2018 |

OTHER PUBLICATIONS

Non-Final Office Action for corresponding U.S. Appl. No. 15/676,571 dated Nov. 16, 2018.

Notice of Allowance for corresponding U.S. Appl. No. 15/676,571 dated Jan. 9, 2019.

International Search Report and Written Opinion for PCT. Application No. PCT/US2018019390 dated May 28, 2018.

International Search Report and Written Opinion for PCT. Application No. PCT/US2016/045690 dated Aug. 5, 2016.

International Search Report and Written Opinion for PCT. Application No. PCT/US2019/064202 dated Dec. 3, 2019.

"Core Specifications" Bluetooth Technology Website; https://www.bluetooth.com/specifications/bluetooth-core-specification/ Last accessed Aug. 19, 2020.

Leach "A Universallyt Unique IDentifier (UUID) URN Napespace" Network Working Group; Jul. 2005 (27 pages).

"Tutorial: How to Create a Custom Bluetooth Smart Embedded Application with the CC2650DK" https://processors.wiki.ti.com; Last accessed Aug. 19, 2020.

"Universally Unique Identifier" Wikipedia; https://en.wikipedia.org/wiki/Universally_unique_identifier; Last accessed Aug. 19, 2020.

* cited by examiner

SYSTEM AND METHODS FOR ESTABLISHING A COMMUNICATION SESSION BETWEEN AN IMPLANTABLE MEDICAL DEVICE AND AN EXTERNAL DEVICE

RELATED APPLICATIONS

This application is a divisional application of U.S. patent application Ser. No. 15/860,507, filed Jan. 2, 2018, which is a continuation of U.S. patent application Ser. No. 15/433,771, filed Feb. 15, 2017 (now U.S. Pat. No. 9,855,433), which is a continuation of U.S. patent application Ser. No. 15/154,787, filed on May 13, 2016 (now U.S. Pat. No. 9,572,992), which is a continuation of U.S. patent application Ser. No. 14/091,809, filed Nov. 27, 2013 (abandoned), entitled "SYSTEM AND METHODS FOR ESTABLISHING A COMMUNICATION SESSION BETWEEN AN IMPLANTABLE MEDICAL DEVICE AND AN EXTERNAL DEVICE," the complete subject matter of which are expressly incorporated herein by reference in their entirety.

BACKGROUND

An implantable medical device ("IMD") is a medical device that is configured to be implanted within a patient anatomy and commonly employ one or more leads with electrodes that either receive or deliver voltage, current or other electromagnetic pulses (generally "energy") from or to an organ or tissue for diagnostic or therapeutic purposes. In general, IMDs include a battery, electronic circuitry, such as a pulse generator and/or a microprocessor that is configured to handle RF communication with an external device as well as control patient therapy. The components of the IMD are hermetically sealed within a metal housing (generally referred to as the "can").

IMDs are programmed by and transmit data to external devices controlled by physicians and/or the patient. The external devices communicate by forming wireless bi-directional communication links with the IMDs. Recently, these external devices may include commercial wireless devices such as tablet computers, smartphones, and the like. For example, a patient may have an IMD that communicates with a tablet computer used by a physician to receive data from and change the settings of the IMD. The table computer receives data from the IMD regarding the patient's physiological state (e.g., the IMD may transmit stored data or sensed physiological parameters). Based on the received data, the physician may adjust the operating parameters of the IMD using the tablet computer.

To initiate the communication link, the IMD and the external device perform a handshaking protocol. During the handshaking protocol, the IMD may have a predetermined timeframe to transmit an invitation data packet and to receive a connection request by the external device. The invitation packet may contain frequency synchronization information, address information, or the like. The external device may receive the invitation data packet and transmit the connection request using the connection specification protocol and data within the invitation data packet (e.g., frequency synchronization information, address information, and the like). If the IMD receives the connection request within the predetermined timeframe the IMD may establish a bi-directional communication link with the external device.

In order for the IMD to do both, transmit the invitation data packet and receive the connection request within the predetermined timeframe, the IMD may have to continually perform the handshaking protocol (e.g., transmit the invitation data packet) regardless of whether the external device is present. By continually transmitting the invitation data packet, the battery life of the IMD may decrease requiring replacement of the IMD. Consequently, there is a need of a method to change the performance of the handshaking protocol by the IMD depending on whether the external device is present or not.

SUMMARY

In accordance with embodiments herein, a method is provided for establishing a communication session with an implantable medical device ("IMD"). The method includes configuring an IMD and an external device to communicate with one another through a protocol that utilizes a dedicated advertisement channel while periodically transmitting, from the IMD, advertisement notices over a dedicated advertisement channel according to the protocol. The advertisement notices being transmitted periodically at an advertisement period. The method further includes repeatedly scanning the advertisement channel, by the external device, for select scanning intervals in search of the advertisement notices, and the scanning operation being repeated periodically at a scan period. The advertisement period and the scan period are independent of one another such that the advertisement and scan period at least partially overlap after a different number of cycles. And the method further includes, when the external device detects one of the advertisement notices, establishing a communications link between the external device and the IMD.

Optionally, the method may include lengthening the scan period in order to shorten the advertisement period.

Optionally, the protocol may include multiple dedicated advertisement channels and multiple data channels.

Optionally, the advertisement notices may be transmitted independently of the select scanning intervals, and the external device acknowledges receipt of the advertisement notice.

Optionally, when the IMD enters an advertising mode, the transmitting operations of the IMD are performed in accordance with a Bluetooth Discovery Service defined within the protocol.

Optionally, the method may include triggering of an advertisement mode when the IMD detects at least one of i) a magnetic field induced upon the IMD, ii) a predetermined vibration scheme, iii) an inductive telemetry signal, or iv) a select RFID signal.

In an embodiment, a communication system is provided. The communication system includes an external device configured to communicate over a wireless protocol that utilizes a dedicated advertisement channel. The external device is configured to repeatedly scan the advertisement channel during a select scan interval such that the scan interval is repeated periodically at a scan period. The communication system includes an IMD configured to communicate over the wireless protocol. The IMD is configured to repeatedly transmit an advertisement notice over the advertisement channel such that the advertisement notice is repeated periodically at an advertisement period over multiple cycles. The advertisement period and the scan period of the communication system are independent of one another, such that the advertisement and scan period at least partially overlap intermittently after a number of cycles. The external device and the IMD are configured to establish a communication link between the IMD and the external device when the external device detects one of the advertisement notices.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

Figure 1:
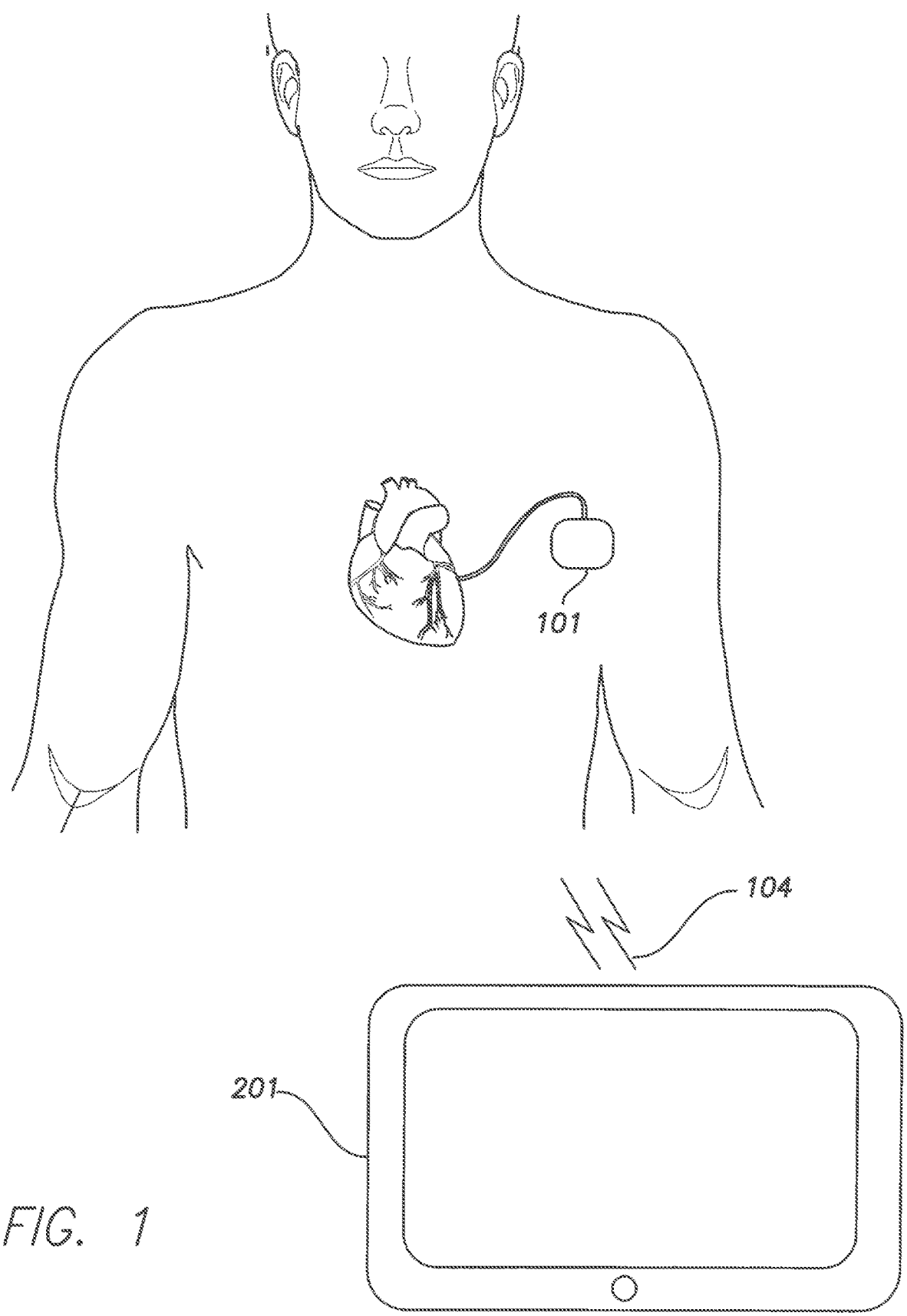
FIG. 1 illustrates a system block diagram of an exemplary system of an embodiment.

FIG. 1 illustrates a simplified block diagram of an IMD 101 and an external device 201 (e.g., table computer, smart phone, laptop, or the like) according to an embodiment of the present subject matter. The IMD 101 may be implanted within a patient. The external device 201 is configured to establish a bi-directional communication link 104 with the IMD 101. The communication link 104 allows the external device 201 to receive measurements from the IMD 101, and to program or send instructions to the IMD 101. The bi-directional communication link 104 may use any standard wireless protocol such as Bluetooth Low Energy, Bluetooth, Wireless USB, Medical Implant Communication Service, WiFi, and the like. The external device 201 may be located within a home of the patient, a hospital, an automobile, at an office of the patient, or the like. The IMD 101 may be one of various types of implantable devices, such as, for example, an implantable pacemaker, implantable cardioverter-defibrillator ("ICD"), defibrillator, cardiac rhythm management ("CRM") device, neurostimulator, electrophysiology ("EP") mapping and radio frequency ("RF") ablation system, or the like.

Figure 2:
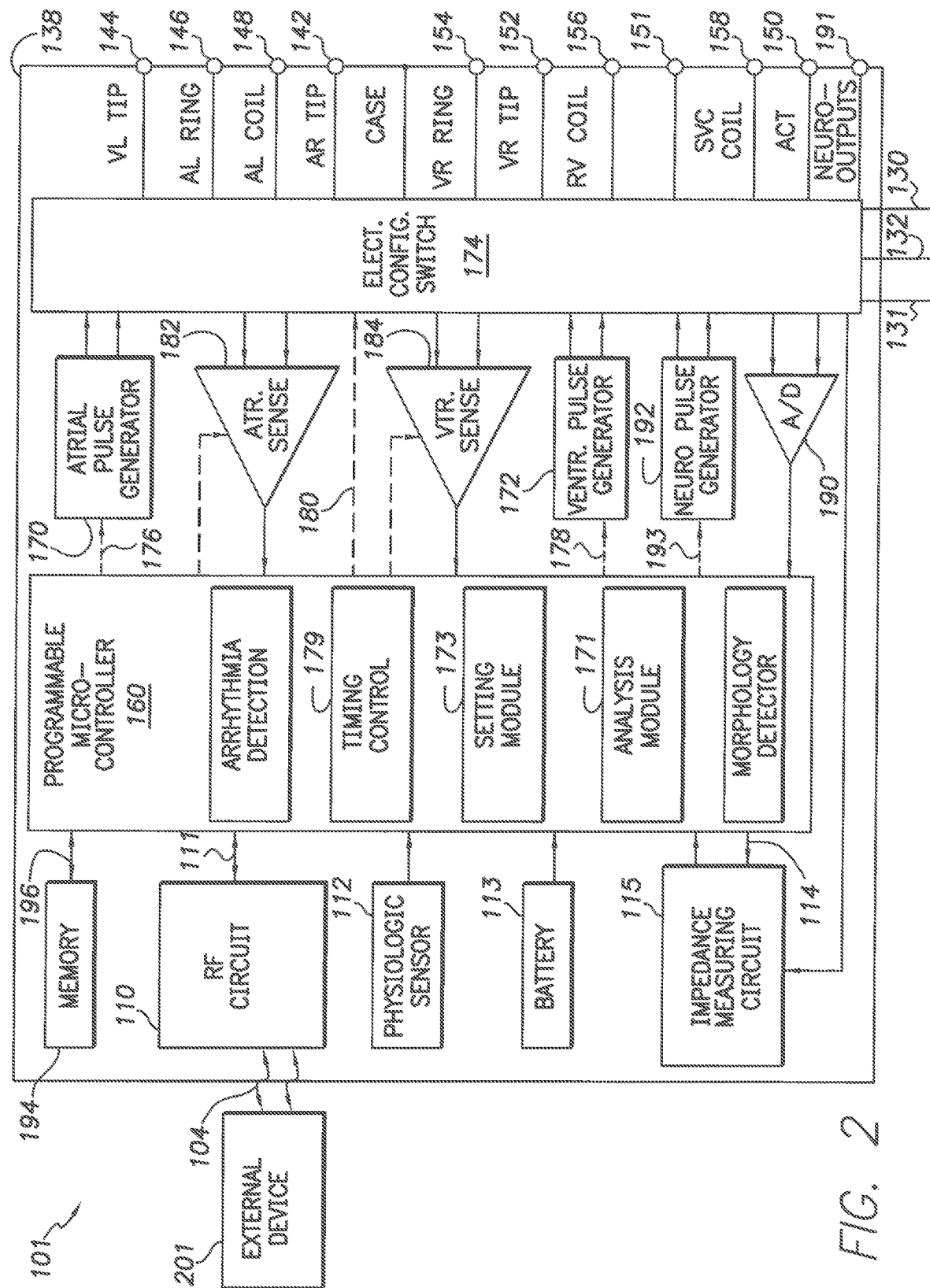
FIG. 2 illustrates a simplified block diagram of an IMD.

FIG. 2 illustrates a block diagram of exemplary internal components of the IMD 101. The systems described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. These devices may be off-the-shelf devices that perform the operations described herein from the instructions described above. Additionally or alternatively, one or more of these devices may be hard-wired with logic circuits to perform these operations.

The IMD 101 is for illustration purposes only, and it is understood that the circuitry could be duplicated, eliminated or disabled in any desired combination to provide a device capable of treating the appropriate chamber(s) with cardioversion, defibrillation and/or pacing stimulation as well as providing for apnea detection and therapy. The housing 138 for IMD 101, shown schematically in FIG. 2, is often referred to as the "can", "case" or "case electrode" and may be programmably selected to act as the return electrode for all "unipolar" modes. The housing 138 may further be used as a return electrode alone or in combination with one or more of the coil electrodes for shocking purposes. The housing 138 further includes a connector (not shown) having a plurality of terminals, 142, 152, 154, 156 and 158 (shown schematically and, for convenience, the names of the electrodes to which they are connected are shown next to the terminals. A right atrial tip terminal ($A_R$ TIP) 142 is adapted for connection to the atrial tip electrode and a right atrial ring terminal may be adapted for connection to right atrial ring electrode. A left ventricular tip terminal ($V_L$ TIP) 144, a left atrial ring terminal ($A_L$ RING) 146, and a left atrial shocking terminal ($A_L$ COIL) 148 are adapted for connection to the left ventricular ring electrode, and a left atrial tip electrode and a left atrial coil electrode respectively. A right ventricular tip terminal ($V_R$ TIP) 152, a right ventricular ring terminal ($V_R$ RING) 154, a right ventricular shocking terminal ($R_V$ COIL) 156, and an SVC shocking terminal (SVC COIL) 158 are adapted for connection to the right ventricular tip electrode, right ventricular ring electrode, an RV coil electrode, and an SVC coil electrode, respectively.

An acoustic terminal (AC T) 150 is adapted to be connected to an external acoustic sensor or an internal acoustic sensor, depending upon which (if any) acoustic sensors are used. Terminal 151 is adapted to be connected to a blood sensor to collect measurements associated with glucose levels, natriuretic peptide levels, or catecholamine levels.

The IMD 101 includes a programmable microcontroller 160 which controls operation. The microcontroller 160 (also referred to herein as a processor module or unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 160 includes the ability to process or monitor input signals (data) as controlled by program code stored in memory. The details of the design and operation of the microcontroller 160 are not critical to the invention. Rather, any suitable microcontroller 160 may be used that carries out the functions described herein. Among other things, the microcontroller 160 receives, processes, and manages storage of digitized cardiac data sets from the various sensors and electrodes. For example, the cardiac data sets may include IEGM data, pressure data, heart sound data, and the like.

The IMD 101 includes an atrial pulse generator 170 and a ventricular/impedance pulse generator 172 to generate pacing stimulation pulses for delivery by the right atrial lead 130, the right ventricular lead 131, and/or the coronary sinus lead 132 via an electrode configuration switch 174. It is understood that in order to provide stimulation therapy in each of the four chambers of the heart, the atrial and ventricular pulse generators, 170 and 172, may include dedicated, independent pulse generators, multiplexed pulse generators or shared pulse generators. The pulse generators, 170 and 172, are controlled by the microcontroller 160 via appropriate control signals, 176 and 178, respectively, to trigger or inhibit the stimulation pulses.

The IMD 101 includes a neuro stimulation pulse generator circuit 192 to generate stimulation pulses for a brain or spinal cord nervous system. The stimulation pulses are delivered by a plurality of electrodes through the neuro output lead 191. The neuro stimulation pulse generator circuit 192 is controlled by the microcontroller 160 via appropriate control signals 193 to trigger or generate the stimulation pulses.

The microcontroller 160 further includes timing control circuitry 179 used to control the timing of such stimulation pulses (e.g., pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. Switch 174 includes a plurality of switches for connecting the desired electrodes to the appropriate I/O circuits, thereby providing complete electrode programmability. Accordingly, the switch 174, in response to a control signal 180 from the microcontroller 160, determines the polarity of the stimulation pulses (e.g., unipolar, bipolar, etc.) by selectively closing the appropriate combination of switches (not shown) as is known in the art.

Atrial sensing circuit 182 and ventricular sensing circuit 184 may also be selectively coupled to the right atrial lead 130, coronary sinus lead 132, and the right ventricular lead 131, through the switch 174 for detecting the presence of cardiac activity in each of the four chambers of the heart. Accordingly, the atrial (ATR SENSE) and ventricular (VTR SENSE) sensing circuits, 182 and 184, may include dedicated sense amplifiers, multiplexed amplifiers or shared amplifiers. The outputs of the atrial and ventricular sensing circuits, 182 and 184, are connected to the microcontroller 160 which, in turn, are able to trigger or inhibit the atrial and ventricular pulse generators, 170 and 172, respectively, in a demand fashion in response to the absence or presence of cardiac activity in the appropriate chambers of the heart.

Cardiac signals are also applied to the inputs of an analog-to-digital (ND) data acquisition system 190. The data acquisition system 190 is configured to acquire IEGM signals, convert the raw analog data into a digital IEGM signal, and store the digital IEGM signals in memory 194 for later processing and/or RF transmission to the external device 201. The data acquisition system 190 is coupled to the right atrial lead 130, the coronary sinus lead 132, and the right ventricular lead 131 through the switch 174 to sample cardiac signals across any combination of desired electrodes. The data acquisition system 190 may also be coupled, through switch 174, to one or more of the acoustic sensors. The data acquisition system 190 acquires, performs A/D conversion, produces and saves the digital pressure data, and/or acoustic data.

The controller 160 controls the acoustic sensor and/or a physiologic sensor to collect heart sounds during one or more cardiac cycles. The heart sounds include sounds representative of a degree of blood flow turbulence. The acoustic sensor and/or physiologic sensor collects the heart sounds that include S1, S2 and linking segments. The S1 segment is associated with initial systole activity. The S2 segment is associated with initial diastole activity. The linking segment is associated with at least a portion of heart activity occurring between the S1 and S2 segments during a systolic interval between the initial systole and diastole activity. The controller 160 changes a value for at least one of the pacing parameters between the cardiac cycles. The controller 160 implements one or more processes described herein to determine values for one or more pacing parameters that yield a desired level of hemodynamic performance.

The controller 160 includes an analysis module 171 and a setting module 173 that function in accordance with embodiments described herein. The analysis module 171 analyzes a characteristic of interest from the heart sounds within at least a portion of the linking segment. The characteristic of interest is indicative of an "amount" of the heart sounds over at least a portion of the systolic interval between the initial systole and diastole activity. The amount of the heart sounds may be derived in different manners, such as determining the energy content, intensity and the like, as well as relations there between. The level of the characteristic changes as the pacing parameter is changed. The setting module 173 sets a desired value for the pacing parameter based on the characteristic of interest from the heart sounds for at least the portion of the linking segment. The pacing parameter may represent at least one of an AV delay, a VV delay, a VA delay, intra-ventricular delays, electrode configurations and the like. The controller 160 changes at least one of the AV delay, the VV delay, the VA delay, the intra-ventricular delays, electrode configurations and like in order to reduce systolic turbulence and regurgitation.

The microcontroller 160 is coupled to memory 194 by a suitable data/address bus 196, wherein the programmable operating parameters used by the microcontroller 160 are stored and modified, as required, in order to customize the operation of IMD 101 to suit the needs of a particular patient. The memory 194 also stores data sets (raw data, summary data, histograms, etc.), such as the IEGM data, heart sound data, pressure data, Sv02 data and the like for a desired period of time (e.g., 1 hour, 24 hours, 1 month). The memory 194 may store instructions to direct the microcontroller 160 to analyze the cardiac signals and heart sounds identify characteristics of interest and derive values for predetermined statistical parameters. The IEGM, pressure, and heart sound data stored in memory 194 may be selectively stored at certain time intervals, such as 5 minutes to 1 hour periodically or surrounding a particular type of arrhythmia of other irregularity in the heart cycle. For example, the memory 194 may store data for multiple non-consecutive 10 minute intervals.

The pacing and other operating parameters of the IMD 101 may be non-invasively programmed into the memory 194 through an RF circuit 110 in bi-directional wireless communication with the external device 201. The RF circuit 110 is controlled by the microcontroller 160 and receives data for transmission by a control signal 111. The RF circuit 110 allows intra-cardiac electrograms, pressure data, acoustic data, Sv02 data, and status information relating to the operation of IMD 101 (as contained in the microcontroller 160 or memory 194) to be sent to the external device 201 through an established bi-directional communication link 104. The RF circuit 110 also allows the external device 201 to program new pacing parameters for the setting module 173 used by the IMD 101.

To establish the communication link 104 between the external device 201 and the IMD 101, the microcontroller 160 instructs the RF circuit 110 to transmit an advertisement notice on an advertisement channel. The advertisement channel is a point to multipoint, unidirectional, channel to carry a repeating pattern of system information messages such as network identification, allowable RF channels to establish the communication link 104, and the like that is included within the advertisement notice. The advertisement notice may be repeatedly transmitted after a set duration or an advertisement period until the communication link 104 is established with the external device 201.

The length of the advertisement period may be adjusted by the microcontroller 160 when entering an advertisement mode. During the advertisement mode, the microcontroller 160 may reduce the length of the advertisement period relative to not being in the advertisement mode. The reduced length of the advertisement period results in the RF circuit 110 transmitting more or an increased number of advertisement notices relative to not being in the advertisement mode. The microcontroller 160 may enter the advertisement mode after detecting a predetermined signal directed at the IMD 101.

The microcontroller 160 supports a particular wireless communication protocol while communicating with the external device 201, such as Bluetooth low energy, Bluetooth, WiFi, Medical Implant Communication Service ("MICS"), WiFi, or the like. Protocol firmware is stored in memory 194, and is accessed by the microcontroller 160 via the data bus 196. The protocol firmware provides the wireless protocol syntax for the microcontroller 160 to assemble data packets, establish communication links, and partition data received from the external device 201.

The IMD 101 may also include an accelerometer or other physiologic sensor 112, commonly referred to as a "rate-responsive" sensor because it is typically used to record the activity level of the patient or adjust pacing stimulation rate according to the exercise state of the patient. Optionally, the physiological sensor 112 may further be used to detect changes in cardiac output, changes in the physiological condition of the heart, or changes in activity (e.g., detecting sleep and wake states) and movement positions of the patient. While shown as being included within IMD 101, it is to be understood that the physiologic sensor 112 may also be external to the IMD 101, yet still be implanted within or carried by the patient. A common type of rate responsive sensor is an activity sensor incorporating an accelerometer or a piezoelectric crystal, which is mounted within the housing 138 of the IMD 101.

The physiologic sensor 112 may be used as the acoustic sensor that is configured to detect the heart sounds. For example, the physiologic sensor 112 may be an accelerometer that is operated to detect acoustic waves produced by blood turbulence and vibration of the cardiac structures within the heart (e.g., valve movement, contraction and relaxation of chamber walls and the like). When the physiologic sensor 112 operates as the acoustic sensor, it may supplement or replace entirely acoustic sensors. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient and, in particular, is capable of detecting arousal from sleep or other movement.

The IMD 101 additionally includes a battery 113, which provides operating power to all of the circuits shown. The IMD 101 is shown as having impedance measuring circuit 115 which is enabled by the microcontroller 160 via a control signal 114. Herein, impedance is primarily detected for use in evaluating ventricular end diastolic volume (EDV) but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 115 is advantageously coupled to the switch 174 so that impedance at any desired electrode may be obtained.

Figure 3:
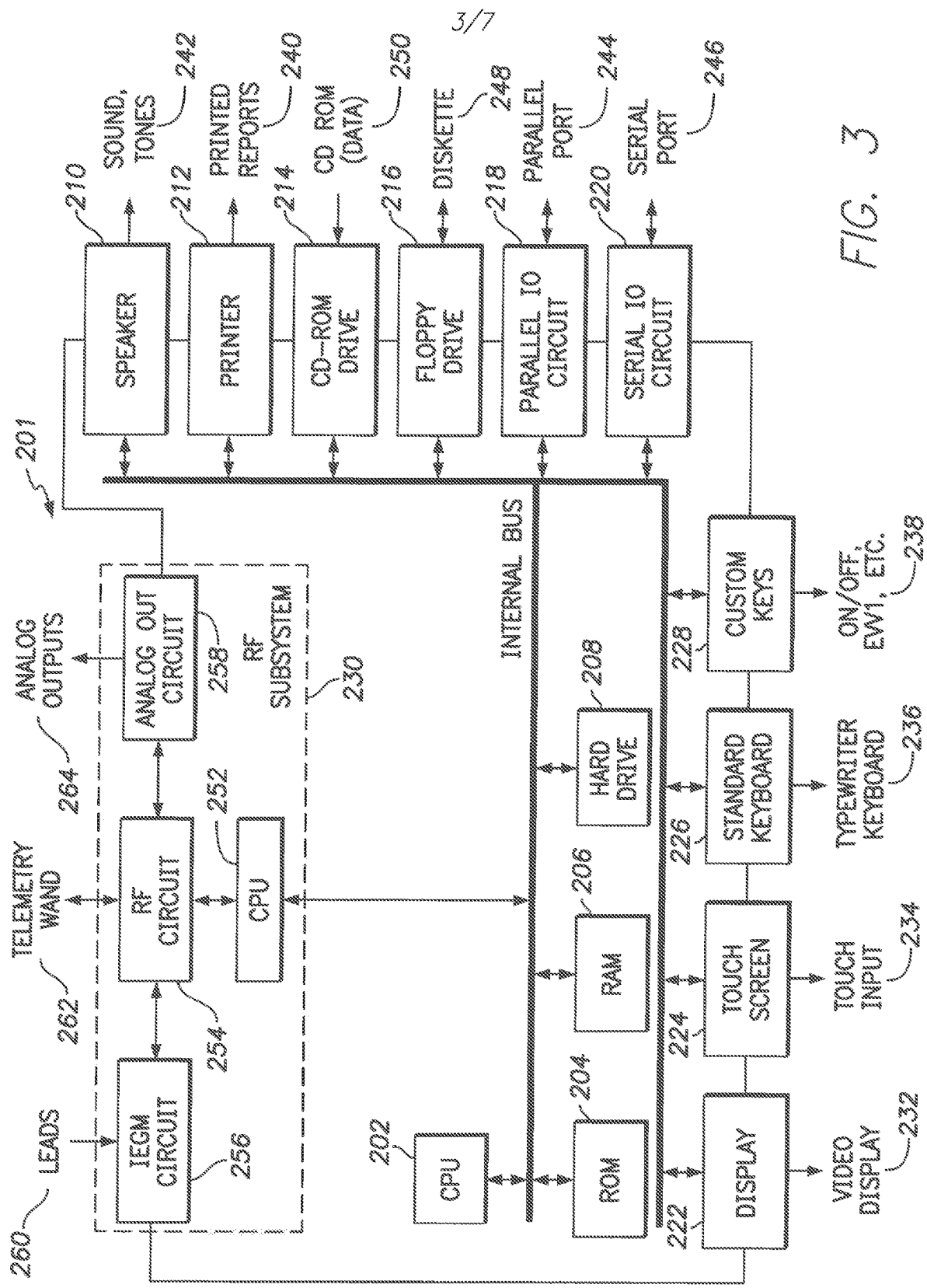
FIG. 3 illustrates a simplified block diagram of an external device.

FIG. 3 illustrates a functional block diagram of the external device 201 that is operated in accordance with the processes described herein and to interface with the IMD 101 as described herein. The external device 201 may be a workstation, a portable computer, a tablet computer, an IMD programmer, a PDA, a cell phone and the like. The external device 201 includes an internal bus that may connect/interface with a Central Processing Unit ("CPU") 202, ROM 204, RAM 206, a hard drive 208, the speaker 210, a printer 212, a CD-ROM drive 214, a floppy drive 216, a parallel I/O circuit 218, a serial I/O circuit 220, the display 222, a touchscreen 224, a standard keyboard 226, custom keys 228, and an RF subsystem 230. The internal bus is an address/data bus that transfers information between the various components described herein. The hard drive 208 may store operational programs as well as data, such as waveform templates and detection thresholds.

The CPU 202 typically includes a microprocessor, a micro-controller, or equivalent control circuitry, designed specifically to control interfacing with the external device 201 and with the IMD 101. The CPU 202 may include RAM or ROM memory, logic and timing circuitry, state machine circuitry, and I/O circuitry to interface with the IMD 101. The display 222 (e.g., may be connected to the video display 232). The touchscreen 224 may display graphic information relating to the IMD 101. The display 222 displays various information related to the processes described herein. The touchscreen 224 accepts a user's touch input 234 when selections are made. The keyboard 226 (e.g., a typewriter keyboard 236) allows the user to enter data to the displayed fields, as well as interface with the RF subsystem 230. Furthermore, custom keys 228 turn on/off 238 (e.g., EVVI) the external device 201. The printer 212 prints copies of reports 240 for a physician to review or to be placed in a patient file, and a speaker 210 provides an audible warning (e.g., sounds and tones 242) to the user. The parallel I/O circuit 218 interfaces with a parallel port 244. The serial I/O circuit 220 interfaces with a serial port 246. The floppy drive 216 accepts diskettes 248. Optionally, the floppy drive 216 may include a USB port or other interface capable of communicating with a USB device such as a memory stick. The CD-ROM drive 214 accepts CD ROMs 250.

The RF subsystem 230 includes a central processing unit (CPU) 252 in electrical communication with an RF circuit 254, which communicates with both an IEGM circuit 256 and an analog out circuit 258. The RF subsystem may be connected to a telemetry wand 262. The circuit 256 may be connected to leads 260. The analog out circuit 258 includes communication circuits to communicate with analog outputs 264. The external device 201 may wirelessly communicate with the IMD 101 and utilize protocols, such as Bluetooth, Bluetooth low energy, WiFi, MICS, and the like. Alternatively, a hard-wired connection may be used to connect the external device 201 to the IMD 101.

Figure 4:
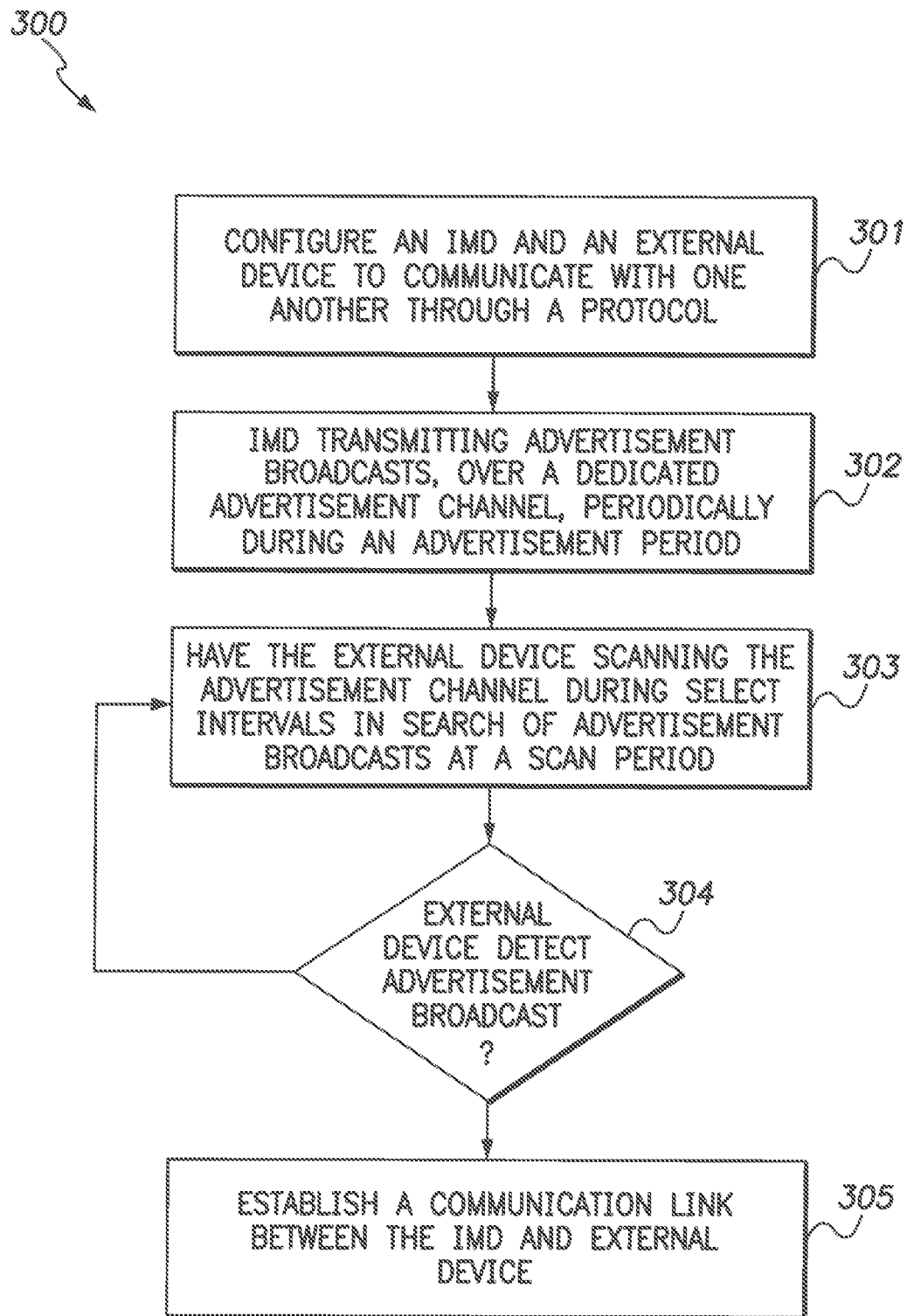
FIG. 4 is a flowchart of a method for establishing a communication session between an IMD and an external device

FIG. 4 illustrates a flowchart of a method 300 for establishing a communication session with an IMD (e.g., 101). The method 300 may be implemented as a software algorithm, package, or system that directs one or more hardware circuits or circuitry to perform the actions described herein. For example, the operations of the method 300 may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

At least one technical effect of at least one portion of the methods described herein includes establishing a communication session with an IMD (e.g., 101) and an external device (e.g., 201) by i) configuring the IMD and the external device to communicate with one another through a protocol that utilizes at least one dedicated advertisement channel, ii) periodically transmit, from the IMD, advertisement notices or packets over the dedicated advertisement channel according to the protocol, wherein the advertisement notices are transmitted periodically at an advertisement period, iii) repeatedly scanning the advertisement channel, by the external device, for select scanning intervals in search of the advertisement notices, the scanning operation being repeated periodically at a scan period, wherein the advertisement period and scan period are independent of one another such that the advertisement and scan periods at least partially overlap intermittently after different number of cycles, and iv) when the external device detects one of the advertisement notices, establishing a communications link between the external device and the IMD.

At 301, the method configures an IMD 101 and an external device 201 to communicate with one another through a protocol. For example, the RF circuit 110 of the IMD 101 and the RF circuit 254 of the external device 201 may be configured to communicate utilizing Bluetooth Low Energy (or Bluetooth Smart), Bluetooth, MICS, WiFi, or the like. Various protocols may be used, provided that the protocol utilizes a dedicated advertisement channel.

The advertisement channel is a point to multipoint, unidirectional, channel. The advertisement channel carries a repeating pattern of system information messages. The system information messages may describe the identity, configuration, and/or available features of the IMD 101. The advertisement channel is used by devices (external device 201, IMD 101) to discover new/other devices, to initiate communication links with other devices, and/or to broadcast connection/address information. The advertisement channel may represent a predetermined bandwidth within an operating frequency range of the protocol. Additionally or alternatively, the advertisement channel may represent a predetermined time slot (e.g., 406 in FIG. 5) with fixed length within a time period (e.g., 405) comprising a plurality of different time slots.

In one embodiment, optionally, the external device 201 and multiple IMDs 101 utilize the Bluetooth Low Energy ("BLE") protocol. The BLE protocol operates within a frequency range of 2400-2483.5 MHz (including guard bands). The operational frequency range is divided into 40 RF channels having a 2 MHz bandwidth. Three RF channels are dedicated advertisement channels having center frequencies at 2402 MHz, 2426 MHz, and 2480 MHz. The remaining RF channels are dedicated data channels. Data channels are utilized by devices having an established BLE communication link to exchange data. For example, the external device 201 has an established communication link with the IMD 101 such that data is exchanged between the external device 201 and the IMD 101 over the data channel. Another IMD, without an established communication link, broadcasts connection/address information along the advertisement channel, for instance at 2404 MHz.

At 302, the IMD 101 transmits one or more advertisement notices, over a dedicated advertisement channel, periodically during an advertisement period. The advertisement notice may be a data packet or a pulse configured to elicit a response from another device to establish a communication link. The advertisement notice may contain frequency synchronization information utilized to form the communication link 104, address information of the IMD 101, address information of the external device 201, and the like. The advertisement notice may be repeated, at a set or variable interval or advertisement period, until the communication link 104 is established. The advertisement period represents the length of time the IMD 101 may transmit another advertisement notice after a previous transmission by the IMD 101 of the advertisement notice. Optionally, the advertisement period may be input by a user (e.g., physician using an external device).

Figure 5:
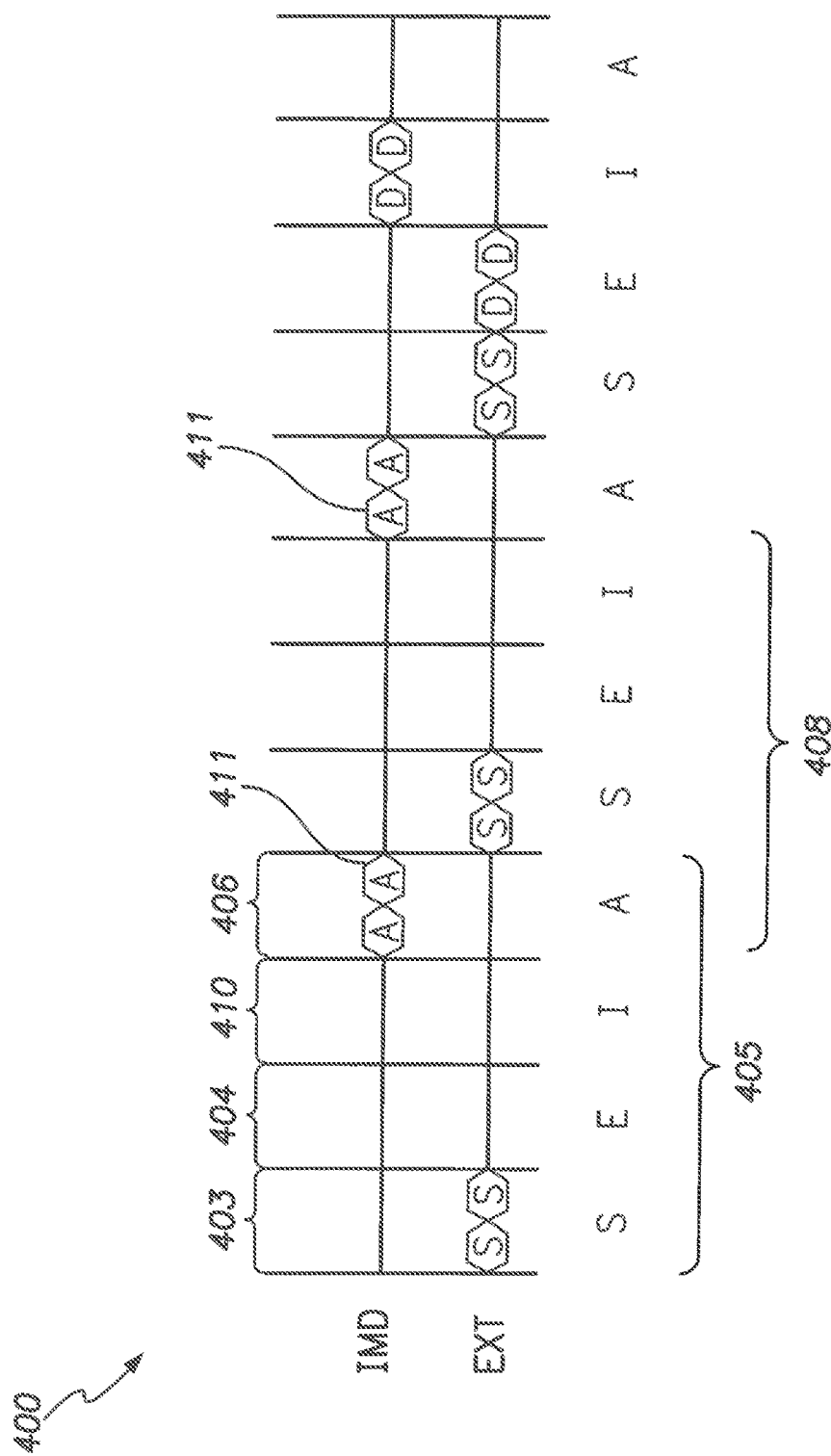
FIG. 5 illustrates a timing signal diagram of an exemplary embodiment of FIG. 1 using a time-multiplexing protocol.

For example, FIG. 5 illustrates a timing signal diagram 400 of an exemplary embodiment having the external device 201 and the IMD 101 using a time-division multiplexing wireless protocol. Under the protocol, the external device 201 and the IMD 101 transmit/receive data along the same frequency band over a repeating time frame 405. The time frame 405 is divided into fixed channels 403, 404, 406, and 410 of a fixed length. The channels may be assigned to a device, or specific functions such as a synchronization channel 403 and an advertisement channel 406. The synchronization channel 403 is used by the external device 201 to transmit a synchronization signal that is used to synchronize other devices within the network to the time frame 405 and channel lengths. The synchronization channel 403 may be predetermined and/or configured by the user (e.g., physician) of the external device 201, such that the length of the timing frame 405 and/or the fixed channels (404, 406, 410) may be extended or shortened.

In one embodiment, optionally, the time frame 405 may have a default length of, for example, 20 ms, and divided into 5 milliseconds (ms) fixed channels (403, 404, 406, 410). The user of the external device 201 may shorten (or lengthen) the time frame 405 to a length of, for example, 12 ms with fixed channel length of 3 ms, and reconfigure the synchronization channel 403 to include the new time frame 405 and fixed channel lengths. The IMD 101 analyzes the synchronization channel 403 containing the current timing specifications with the reconfigured advertisement channel 406, and updates the timing specification on the protocol syntax stored in the memory 194. The IMD 101 transmits an advertisement notice 411 along the reconfigured advertisement channel 406 to form a communication link 104 with the external device 201. The IMD 101 may continually retransmit the advertisement notice 411 over the advertisement channel 406 until the communication link 104 is established. The retransmission of the advertisement notice 411 occurs at the beginning of every advertisement period 408 or, using the above example, every 12 ms, such that, the advertisement notice 411 is repeatedly transmitted during the advertisement channel 406.

Once the external device 201 receives the advertisement notice 411, the external device 201 may transmit the data channel specifications for the IMD 101 on the data channel 404 to establish the communication link 104 between the external device 201 and the IMD 101.

At 303, the external device 201 scans the advertisement channel during select intervals in search of one or more advertisement notices. The external device repeats the scan periodically at a scan period. The external device 201 monitors or scans the advertisement channel for advertisement notices using the RF circuit 254.

Figure 6A:
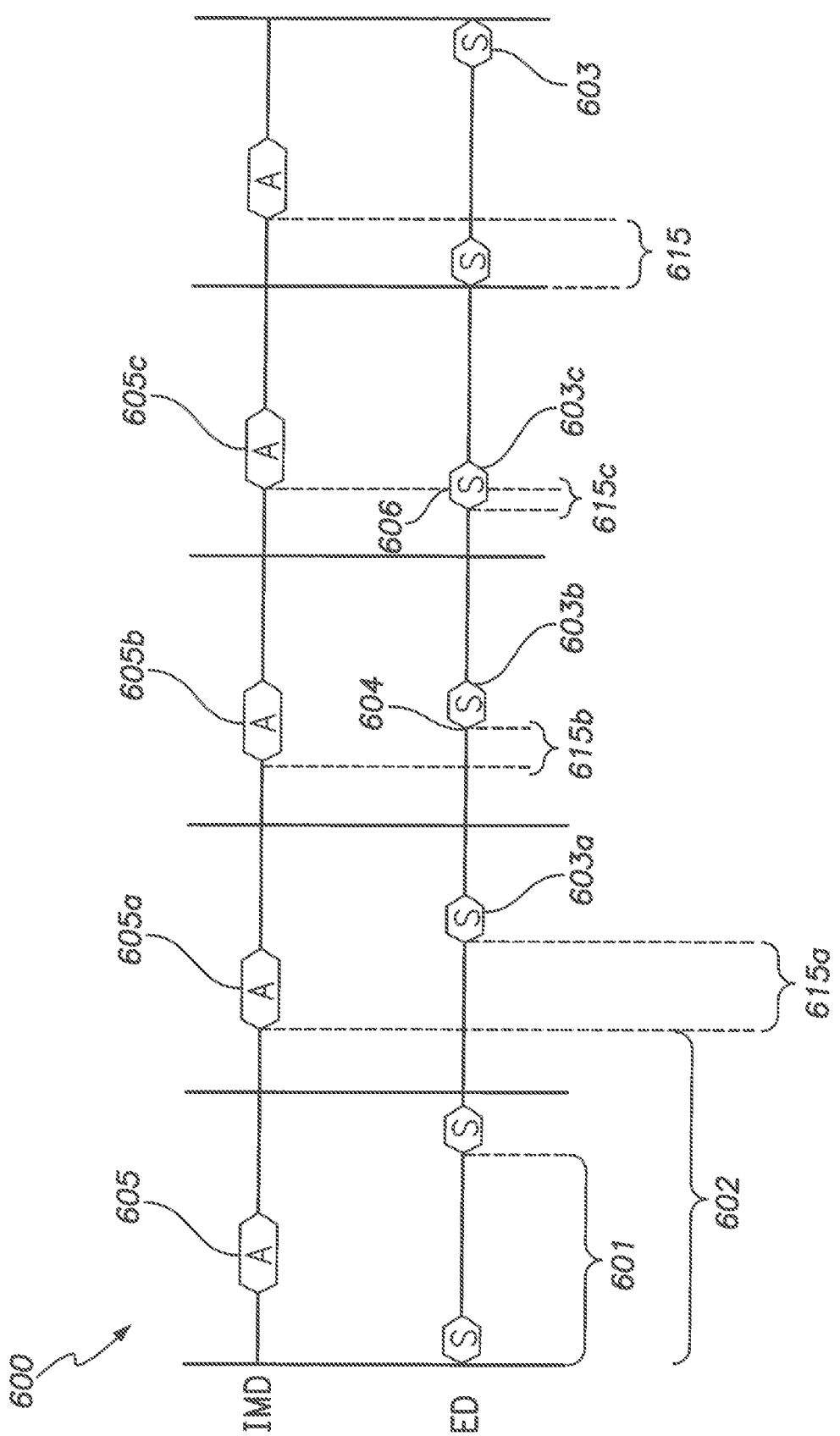
FIG. 6a illustrates a timing signal diagram of an exemplary embodiment of FIG. 1 using a specified frequency for an advertisement channel.

For example, FIG. 6a illustrates a timing diagram 600 of an exemplary embodiment having the external device 201 and the IMD 101 using a wireless protocol that utilizes a specified frequency for an advertisement channel. The IMD 101 is transmitting an advertisement notice 605 on the advertisement channel using the RF circuit 110. The advertisement period 602, for example, may be 5 seconds (s) such that the advertisement notice 605 may be repeated every 5 s. Optionally, the advertisement period 602 may be longer or shorter than the above example. Additionally or alternatively, the advertisement period may be predetermined and stored in memory 194 of the IMD 101.

The user, using the touchscreen 224 or standard keyboard 236, may instruct the external device 201 to establish the communication link 104 with the IMD 101. The CPU 202 instructs the RF subsystem 230 to output the received transmissions from the advertisement channel (e.g., 2402 MHz, 2426 MHz, 2480 MHz), for example, every 1 s. The output of the RF subsystem 230 corresponds to a scanning interval 603. The RF subsystem repeats the scanning interval 603 every scan period 601 such that the scanning interval 603 may be repeated, for example, every 4 s. The scanning interval 603 and/or scan period 601 may be longer or shorter than the above example. Additionally or alternatively, the scanning interval 603 and/or scan period 601 may be a predetermined length stored on the ROM 204, the RAM 206, or the hard drive 208. Optionally, the scanning interval 603 and/or scan period 601 is configured by the user, such that, the interval 603 or period 601 may be increased or decreased. The RF subsystem 230 continually repeats the scanning interval 603 until the CPU 202 acknowledges receipt of the advertisement notice 605.

The scan period 601 and the advertisement period 602 occur independent and asynchronous with respect to one another, such that the advertisement notices 605 intermittently overlap the scan intervals at 604 and 606. Each period length is predetermined from distinct and separate sources. The scan period 601 is predetermined or configured by the user of the external device 201. Separately, the advertisement period 602 is predetermined by the protocol syntax stored in the memory 194 of the IMD 101. One of the scan period 601 and the advertisement period 602 may be altered, while, the length of the other period (e.g., advertisement period 602, scan period 601) remains constant.

The scan period 601 has an asynchronous phased relation with respect to the advertisement period 602 in order that a phase interval 615 between beginnings of the scanning intervals 603 and advertisement notices 605 continuously (or intermittently) changes.

For example, the scan period 601 may be 4 s having the scanning interval 603 of 1 s, and advertisement period 602 may be 5 s having the advertisement notice 605 of 1.5 s. The different lengths of the periods 601 and 602 represent the asynchronous phased relationship with respect to each other. The asynchronous phased relationship causes the advertisement notice 605 and the scanning interval 603 to begin at different times thus creating phase intervals 615. The length of the phase interval 615 can be extended or shortened by changing the advertisement period 602 of the IMD 101 or the scan period 601 of the external device 201. Thus, by configuring the advertisement period 602 or the scan period 601, the phase interval 615 may continuously change or be changed intermittently after a set number of cycles. The beginning of the cycle occurs at the transmission of the advertisement notice 605 or the scan interval 603. The phase interval 615 may be controlled by the user changing the scan period 603 of the external device 201 or by the microcontroller 160 changing the advertisement period 602 of the IMD 101.

For example, the phase interval 615 of the timing diagram 600, is continuously changing after each cycle. The phase interval 615a, measured between the beginning of the advertisement notice 605a and the beginning of the scan interval 603a, may be approximately 1.5 s long. The advertisement notice 605a and the scanning interval 603a do not partially overlap. The phase interval 615b, between the advertisement notice 605b and the scanning interval 603b, may be approximately 750 ms long. The phase interval 615c, between the advertisement notice 605c and the scanning interval 603c, may be approximately 250 ms long. Accordingly, the length of the phase interval 615 continuously changes each cycle. The changes in the length of the phase interval 615 illustrate that each cycle or repetition of the scanning interval 603 and the advertisement notice 605 shifts with respect to each other allowing for partially overlapping events at 604 and 606 to occur. For instance, only the phase intervals 615b-615c are associated with partially overlapping advertisement notices 605b-c and scanning intervals 615b-c. Although the periods 601, 602 are asynchronous, the scanning intervals 602 and the advertisement notices 605 will partially overlap and enable the external device 201 intermittently or after a set number of cycles to receive the advertisement notice 605. The overlaps occur intermittently, in that after a number of cycles the interval 603 and notice 602 will partially overlap in fewer cycles than the number of cycles. For example, the interval 603 and notice 602 partially overlap after the fourth and fifth cycle of the scanning interval 603 or the third and fourth cycle of the advertisement notice 605.

Optionally, the IMD 101 may have an advertisement mode that decreases the number of cycles needed until the communication link 104 is established, by increasing the likelihood of the scanning interval 603 partially overlapping the advertisement notice 605. During an advertisement mode, the microcontroller 160 may decrease the length of the advertisement period 602, relative to not being in the advertisement mode, thus, increasing the number of advertisement notices 605 in a time frame 609. The increased number of advertisement notices 605 increase the number of partial overlaps with the scanning intervals 603, allowing the external device 201 to detect or receive the advertisement notice 605 in a shorter amount of cycles relative to the IMD 101 not being in an advertisement mode.

Figure 6B:
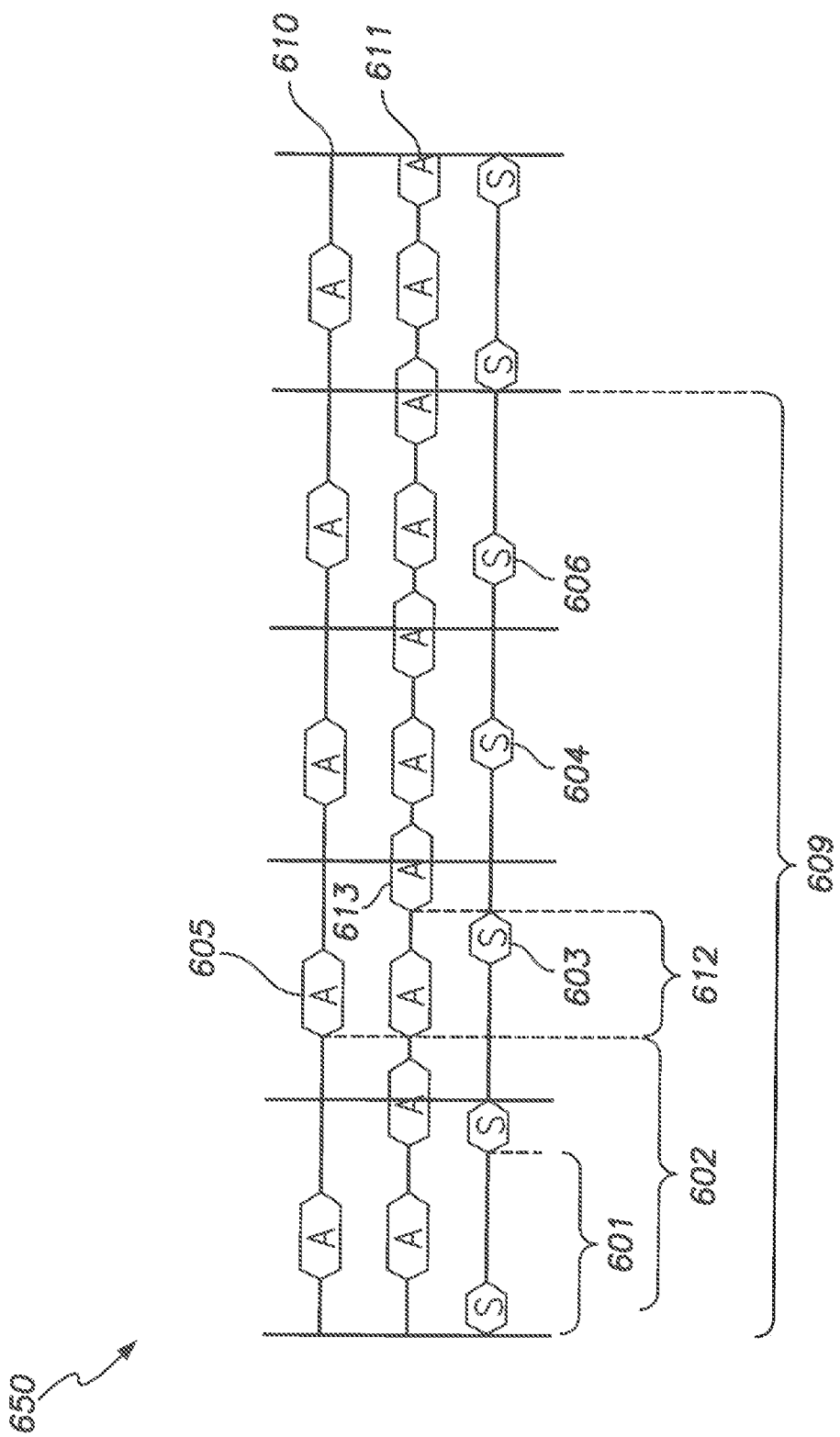
FIG. 6b illustrates a timing signal diagram of an exemplary embodiment of FIG. 1 using a specified frequency for an advertisement channel.

For example, FIG. 6b illustrates a timing diagram 650 of an exemplary embodiment having the external device 201 and IMD 101 using a wireless protocol that utilizes a specified frequency for the advertisement channel. The external device 201 is repeatedly scanning the advertisement channel, such that, the scan period 601 of the scanning interval 603, for example, may be 4 s. Optionally, the scan interval 603 may be longer or shorter than that illustrated in FIG. 6b. The IMD 101 operates in two modes, a default mode 610 and the advertisement mode 611. The advertisement notices 605 and 613 for each mode 610 and 611 is illustrated in timing diagram 650.

When the IMD 101 is in the default mode 610, the IMD 101 transmits the advertisement notice 605 repeatedly such that the advertisement period 602, for example, may be 5 s. The advertisement notices 605 and the scanning intervals 603 partially overlap after approximately 12 s and 17 s, or at the fourth and fifth cycles of the scanning interval 603.

When the IMD 101 is in the advertisement mode 611, the advertisement period may be reduced, for example, to 2.5 s. The reduced advertisement period 612 increases the number of advertisement notices 613 transmitted by the IMD 101 than in the default mode 611 during the same period. Such that after, for example, 20 s (the time period 609), the IMD 101 in the advertisement mode will have had eight cycles or transmitted eight advertisement notices 613 while only four advertisement notices 605 would have been transmitted in the default mode 610. While in the advertisement mode 611, the advertisement notices 613 and the scanning intervals 603 partially overlap, for example, after approximately 4 s, 12 s, 17 s, or at the second, fourth, and fifth cycle of the scanning interval 603. Thus, the IMD 101 operating in the advertisement mode 611 allows the external device 201 to receive the advertisement notice 605 in a shorter amount time and with more partial overlaps relative to the IMD 101 not being in an advertisement mode 611.

At 304, the method determines whether the external device 201 detects the advertisement notice. For example, the external device 201 receives the advertisement notice in the form of a data packet transmitted from a remote device. The CPU 202 analyzes or compares the data packet with the protocol syntax stored on the ROM 204, the RAM 206, or the hard drive 208. The protocol syntax may include the structure of an advertisement notice (e.g., data packet specifications, appropriate number of bits, frequency, or the like) utilized by the wireless protocol. Optionally, the advertisement notice may include a unique code designating the packet as an advertisement. By comparing the protocol syntax with the data packet, the CPU 202 determines whether the received data packet is an advertisement notice using the wireless protocol of the external device 201. If the received data packet is determined not to be an advertisement notice, the external device 201 may continue scanning the advertisement channel.

In one embodiment, optionally, the external device may acknowledge receipt of the advertisement notice. For example, when the CPU 202 determines that the data packet received by the RF circuit 254 is the advertisement notice 605, the CPU 202 may output an acknowledgment receipt (e.g., data packet) to be transmitted by the RF circuit 254 along the advertisement channel. The acknowledgment receipt may include address information of the external device 201 and/or the IMD 101, or a request for further information or data from the IMD 101 to establish the communication link 104 (e.g., transceiver identification, patient identification, frequency information, or the like).

At 305 the method establishes a communication link between the IMD 101 and the external device 201. The communication link 104 is established once data is exchanged between the IMD 101 and the external device 201.

For example, the advertisement notice 605 may contain specifications for the frequency and/or timing specifications for the data channel to exchange data with the IMD 101. Once the CPU 202 of the external device 201 determines the advertisement notice has been received, the CPU 202 will partition the data channel and the address of the IMD 101 from the advertisement notice. The CPU 202 constructs a data packet by adding packet frames to conform to the protocol such as the address of the IMD 101 and/or external device 201, error detection codes such as CRC, a payload, or the like. The payload may include instructions and/or measurement requests from the user intended for the IMD 101. Once the data packet has been formed, the CPU 202 outputs the data packet to the RF subsystem 230 to be transmitted along the data channel to the IMD 101.

The RF circuit 110 receives the data packet and outputs to the microcontroller 160. The microcontroller 160 may store the data packet in memory 194 for analysis. The microcontroller 160 determines whether the data packet is in response to the advertisement notice 605 by comparing the address information of the data packet with the address transmitted by the IMD 101 within the advertisement notice 605. If the address information matches, the microcontroller 160 partitions the payload from the data packet and carries out the instructions of the payload by comparing the instructions to the stored instruction set on the memory 194. Optionally, the microcontroller 160 may compare the address information of the external device 201 on the data packet with a permissible links table stored in memory 194 to determine whether the IMD 101 should ignore or partition the payload of the data packet. Once the microcontroller 160 completes the requested instructions, the microcontroller 160 constructs a responsive data packet to the external device 201 conforming to the protocol. Once the responsive data packet is constructed, the microcontroller 160 outputs the responsive data packet to the RF circuit 110 establishing the communication link 104 with the external device 201.

In one embodiment, optionally, when the IMD 101 enters into the advertisement mode, the transmitting operations of the protocol utilized by the IMD 101 are in accordance with the Bluetooth Discovery Service used by the Bluetooth and/or BLE protocol. The Bluetooth and BLE protocols are defined within "Bluetooth Specification Version 4.0 [Vol 0], published Jun. 30, 2011 (incorporated herein by reference).

For example, the microcontroller 160 triggers the IMD 101 into the advertisement mode by constructing the advertisement notice in accordance with the Bluetooth Discovery Service used by the BLE protocol. The advertisement notice contains a preamble, an access address, a protocol data unit ("PDU"), and a CRC. The preamble and access address are predetermined eight and 32 bit values that may be stored on the memory 194. The PDU contains a 16 bit header and a variable sized payload. The payload contains the address field for the IMD 101.

Once the advertisement notice is constructed, the microcontroller 160 may output the advertisement notice to the RF circuit 110 for transmission on the advertisement channel having a center frequency at 2402 MHz, 2426 MHz, or 2480 MHz. The advertisement period may be less than or equal to 10 ms or may be a predetermined length stored on the memory 194.

The microcontroller 160 will instruct the RF circuit 110 to monitor for requests by the external device 201 on the advertisement channel of the transmitted advertisement notice. If no request is received by the RF circuit 110 by the end of the advertisement period, the microcontroller 160 may instruct the RF circuit 110 to transmit another advertisement notice on the same or another advertisement channel. Alternatively, if the RF circuit 110 receives a connection request from the external device 201 containing the address of the IMD 101, the microcontroller 160 may establish a communication link 104 with the external device 201.

In one embodiment, optionally, the IMD 101 enters into the advertisement mode when the IMD 101 detects an induced magnetic field upon the IMD 101. A magnetic sensor such as a hall sensor, MEMS sensor, or the like may be operatively coupled to the A/D data acquisition system 190 of the IMD 101. The A/D data acquisition system 190 measures and stores the output of the magnetic sensor. The A/D data acquisition system 190 compares the stored measurements for sudden changes in the magnetic field of the IMD 101, such that, the A/D data acquisition system 190 detects whether a magnetic field is induced upon the IMD 101. Once the magnetic field is detected, the A/D data acquisition system 190 outputs a detection signal to the microcontroller 160. The microcontroller 160 responds by triggering the IMD 101 into the advertisement mode.

The magnetic field may be induced by the user (e.g., patient, physician) of the external device 201 intending to establish the communication link 104 between the external device 201 and the IMD 101. Optionally, a solenoid may be coupled to the external device 201, allowing the user to induce the magnetic field upon the IMD 101 from the external device 201.

In one embodiment, optionally, the IMD 101 may enter into the advertisement mode when the IMD 101 detects a predetermine vibration scheme. The vibration scheme may be a signal output to a vibration motor coupled to the external device 201 that corresponds to a speed and/or pattern. The vibration motor may be a DC motor with an offset mass or weight attached to the shaft. Once the signal output is received by the vibration motor, the vibration motor spins the shaft at a speed and/or direction that corresponds to the signal output. The offset mass on the shaft causes the motor to be displaced or vibrate. The signal output may be activated by the user of the external device 201 intending to establish the communication link 104 by using the touchscreen 224, the standard keyboard 226, or custom keys 228. The CPU 202 retrieves the vibration scheme from the ROM 204, the RAM 206, the hard drive 208 corresponding to the connection instruction from the user. The CPU 202, through the Serial I/O Circuit 220, outputs the signal output to the vibration motor. The vibration motor is placed on or near the IMD 101 such that the vibration motor causes the IMD 101 to be displaced by the vibrations of the vibration motor.

The physiologic sensor 112, configured as the accelerometer, of the IMD 101 detects the displacement or changes in position of the IMD 101 from the vibrations. The physiologic sensor 112 outputs position measurements of the IMD 101 to the microcontroller 160. The microcontroller 160 may compare the changes in the position measurements to determine a speed or pattern which will correspond to the vibration scheme from the vibration motor. The microcontroller 160 compares the measured vibration scheme to a predetermined vibration scheme stored on the memory 194. Once the microcontroller 160 determines that the two vibration schemes are approximately similar within a set threshold or error rate, the microcontroller 160 triggers the IMD 101 into the advertisement mode. The set threshold may be a predetermined amount stored on the memory 194.

In one embodiment, optionally, the IMD 101 may enter into the advertisement mode when the IMD 101 detects an inductive telemetry signal. For example, the telemetry wand 262 of the external device 201 may include an inductor coil circuitry. The RF circuit 110 of the IMD 101 may be configured with an inductive telemetry antenna. Once the user instructs the external device 201 to form the connection link 104 with the IMD 101, the CPU 202 outputs a corresponding telemetry signal stored on the ROM 204, the RAM 206, or the hard drive 208 to the RF subsystem 230. The telemetry signal, transmitted by the telemetry wand 262, changes the inductive coupling between the telemetry wand 262 and the inductive telemetry antenna of the RF circuit 110. The microcontroller 160 measures an electrical change caused by the inductive coupling, such as a voltage or a current change from the output of the RF circuit 110, to determine the telemetry signal. The microcontroller 160 compares the measured telemetry signal with a predetermined telemetry signal stored in memory 194. Once the microcontroller 160 determines that the telemetry signals are approximately similar within a set threshold, the microcontroller 160 triggers the IMD 101 into the advertisement mode.

In one embodiment, optionally, the IMD 101 may enter into the advertisement mode when the IMD 101 detects a select RFID signal. For example, the RF subsystem 230 includes an RFID circuit. The RFID circuit transmits a predetermined identification signal that corresponds to the external device 201. The identification signal may be stored on the ROM 204, the RAM 206, the hard drive 208, or an internal memory of the RFID circuit. Alternatively or additionally, the identification signal may be input by the user using the touchscreen 224, standard keyboard 226, or custom keys 228.

The user instructs the external device 201 to form a connection link 104 with the IMD 101. The CPU 202 initiates the communication link instructions, by outputting the identification signal to be transmitted by the RFID circuit. Once the identification signal is received by the IMD 101, the RF circuit 110 outputs the identification signal to the microcontroller 160. The microcontroller 160 determines whether to enter into an advertisement mode by comparing the identification signal with stored identification signals on memory 194. The stored identification signals may be a table or list of all external devices that may form a communication link 104 with the IMD 101. Once the microcontroller 160 finds a match for the identification signal, the microcontroller 160 triggers the IMD 101 into the advertisement mode.

The memory 194 may include or represent one or more memories (e.g., a tangible and non-transitory computer readable memory, such as a computer hard drive, EEPROM, ROM, RAM, or the like) having a table, list, database, or other memory structure used to store information used in conjunction with performing one or more of the methods described herein.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hardwired to perform the methods or portions of the methods described herein, and/or when the processors (e.g., of the devices described herein) operate according to one or more software programs that are written by one or more persons of ordinary skill in the art to perform the operations described in connection with the methods.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

What is claimed is:

1. An implantable medical device (IMD), comprising:
   memory configured to store program code;
   a processor that, when executing the program code, is configured to:
      at least one of i) analyze signals indicative of cardiac activity or ii) deliver a therapy;
      construct an advertisement notice that includes a protocol data unit (PDU) payload;
      insert, into the advertisement notice, information associated with at least one of an address, identity, configuration, status or feature of the IMD;
      repeatedly transmit the advertisement notice over an advertisement channel at an advertisement period; and
      establish a communication link with an external device.

2. The IMD of claim 1, wherein the advertisement period is independent from a scan period utilized by the external device such that the transmission of the advertisement notice and scan period at least partially overlap intermittently after a number of cycles.

3. The IMD of claim 1, wherein the wireless protocol utilizes multiple dedicated advertisement channels and multiple data channels.

4. The IMD of claim 1, wherein the wireless protocol constitutes a Bluetooth low energy protocol.

5. The IMD of claim 1, wherein the processor is further configured to transmit, to the external device, at least one of intra-cardiac electrograms, pressure data, acoustic data, Sv02 data, and status information relating to operation of the IMD.

6. The IMD of claim 1, wherein the information inserted into the advertisement notice includes status information relating to operation of the IMD.

7. The IMD of claim 1, wherein the processor is further configured to include, in the advertisement notice, at least one of a frequency synchronization information related to a communications link, address information of the IMD, or address information of the external device.

8. The IMD of claim 1, wherein the processor is further configured to:
   construct the advertisement notice to include at least two of preamble, access address, PDU header or, one or more PDU payload fields; and
   include the information into a select one of the preamble, access address, PDU header or, one or more PDU payload fields based on a type of the information.

9. The IMD of claim 8, wherein the processor is further configured to include the status information, relating to operation of the IMD, in the select one of the preamble, access address, PDU header or, one or more PDU payload fields.

10. The IMD of claim 1, wherein the processor is further configured to: receive a data packet from the external device, determine whether the data packet is in response to the advertisement notice, and based thereon, establish the communication session.

11. The IMD of claim 1, wherein the communications session includes at least one of: i) transmit, over the communications link, the signals; or ii) receive, over the communication link, one or more parameters to control the analysis or signals or the delivery of the therapy.

12. The IMD of claim 1, wherein the processor is further configured to enter an advertisement mode when the IMD detects at least one of i) a magnetic field induced upon the IMD, ii) a predetermined vibration scheme, iii) an inductive telemetry signal, or iv) a select RFID signal.

13. A method for establishing a communications session with an implantable medical device (IMD), wherein the IMD and an external device are configured to communicate with one another through a protocol that utilizes a dedicated advertisement channel, the method comprising:
under the control of one or more processors,
at least one of i) analyzing signals indicative of cardiac activity or ii) delivering a therapy;
constructing an advertisement notice that includes a protocol data unit (PDU) payload;
inserting, into the advertisement notice, information associated with at least one of an address, identity, configuration, status or feature of the IMD;
repeatedly transmitting the advertisement notice over an advertisement channel at an advertisement period; and
establishing a communication link with the external device.

14. The method of claim 13, further comprising managing the advertisement period to be independent from a scan period utilized by the external device such that the transmission of the advertisement notice and scan period at least partially overlap intermittently after a number of cycles.

15. The method of claim 13, wherein the wireless protocol utilizes multiple dedicated advertisement channels and multiple data channels.

16. The method of claim 13, wherein the wireless protocol constitutes a Bluetooth low energy protocol.

17. The method of claim 13, wherein the at least one of the address, identity, configuration or feature of the IMD includes status information relating to operation of the IMD.

18. The method of claim 13, further comprising:
constructing the advertisement notice to include at least two of preamble, access address, protocol data unit (PDU) header or, one or more PDU payload fields; and
including the information into a select one of the preamble, access address, PDU header or, one or more PDU payload fields based on a type of the information.

19. The method of claim 18, further comprising including the status information, relating to operation of the IMD, in the select one of the preamble, access address, PDU header or, one or more PDU payload fields.

20. The method of claim 13, further comprising: receiving a data packet from the external device; determining whether the data packet is in response to the advertisement notice; and based thereon, establishing the communication session.

* * * * *